United States Patent [19]

Bokel

[11] Patent Number: 4,762,933

[45] Date of Patent: Aug. 9, 1988

[54] 1-OXA-2-OXO-3-R-3-AZA-5-Z-CYCLOPENTANE DERIVATIVES

[76] Inventor: Heinz-Hermann Bokel, Duererstrasse 30, D-6100 Darmstadt, Fed. Rep. of Germany

[21] Appl. No.: 886,492

[22] Filed: Jul. 17, 1986

[30] Foreign Application Priority Data

Jul. 18, 1985 [DE] Fed. Rep. of Germany ....... 3525648

[51] Int. Cl.$^4$ .......................................... C07D 263/04
[52] U.S. Cl. .................................................. 548/229
[58] Field of Search ........................................ 548/229

[56] References Cited

U.S. PATENT DOCUMENTS

| | | | |
|---|---|---|---|
| 3,120,510 | 2/1964 | Steyermark | 548/229 |
| 3,413,198 | 11/1968 | Deutsch et al. | 195/103.5 |
| 3,451,935 | 6/1969 | Roald et al. | 252/135 |
| 3,539,450 | 11/1970 | Deutsch et al. | 195/68 |
| 3,687,717 | 8/1972 | Philip et al. | 117/100 |
| 3,687,853 | 8/1972 | Natali et al. | 252/89 |
| 3,721,725 | 3/1973 | Briggs et al. | 264/6 |
| 4,106,991 | 8/1978 | Markussen et al. | 195/63 |
| 4,242,219 | 12/1980 | Bogerman et al. | 252/174.12 |
| 4,428,973 | 1/1984 | Horner et al. | 427/3 |
| 4,447,527 | 5/1984 | Monte et al. | 435/7 |
| 4,489,026 | 12/1984 | Yalkowsky et al. | 264/123 |
| 4,572,897 | 2/1986 | Amotz et al. | 435/177 |

OTHER PUBLICATIONS

Tsuda et al., Chem. Pharm. Bull., vol. 29 (1981), pp. 3593–3600.

*Primary Examiner*—Donald G. Daus
*Assistant Examiner*—Cecilia Shen
*Attorney, Agent, or Firm*—Millen & White

[57] ABSTRACT

New 1-oxa-2-oxo-3-R-3-aza- 5-Z-cyclopentane derivatives, wherein

R is alkyl or hydroxyalkyl having in each case 1–6 C atoms, cycloalkyl having 3–8 C atoms, unsubstituted aryl or aralkyl or aryl or aralkyl each of which has a total of 6–15 C atoms and, in the aryl radical, is monosubstituted to trisubstituted by alkyl, alkoxy, OH and/or Cl or monosubstituted by methylenedioxy, Z is —(CHOH)$_n$—H and n is 2, 3, 4 or 5, can be used as intermediate products for the preparation of active compounds for medicaments, such as toloxatone.

15 Claims, No Drawings

1-OXA-2-OXO-3-R-3-AZA-5-Z-CYCLOPENTANE DERIVATIVES

BACKGROUND OF THE INVENTION

This invention relates to new 1-oxa-2-oxo-3-R-3-aza-5-Z-cyclopentane derivatives (I). Similar compounds are described in U.S. Pat. No. 3,120,510.

SUMMARY OF THE INVENTION

It is an object of this invention to provide such compounds.

Upon further study of the specification and appended claims, further objects and advantages of this invention will become apparent to those skilled in the art.

These objects have been achieved by providing new 1-oxa-2-oxo-3-R-3-aza-5-Z-cyclopentane derivatives (I) wherein:

R is alkyl or hydroxyalkyl having in each case 1-6 C atoms, cycloalkyl having 3-8 total C atoms (optionally substituted by alkyl), unsubstituted aryl or aralkyl each of 6-15 C atoms in total or aryl or aralkyl each of which has a total of 6-15 C atoms and, in the aryl radical, is monosubstituted to trisubstituted by alkyl (e.g., of 1-6 C atoms), alkoxy (e.g., of 1-6 C atoms), OH and/or Cl or monosubstituted by methylenedioxy, Z is $-(CHOH)_n-H$ and n is 2, 3, 4 or 5.

DETAILED DESCRIPTION

The compounds I can be prepared by reacting a compound of the formula $R-NH-CH_2-CHOH-Z$ (II) with a reactive derivative of carbonic acid.

Compounds of the formula II are in part known and all can be conventionally obtained, for example, by reacting amines of the formula $R-NH_2$ with aldehydes of the formula $Z-CHOH-CHO$ and by subsequently or simultaneously reducing the resulting Schiff's bases or half-aminals of the formlae

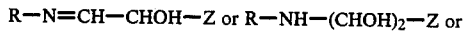
R—N=CH—CHOH—Z or R—NH—(CHOH)₂—Z or

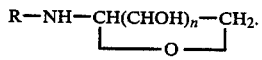

Suitable examples of amines of the formula R—NH₂ are methylamine, ethylamine, propylamine, isopropylamine, butylamine, isobutylamine, sec.-butylamine, tert.-butylamine, pentylamine, 1-ethylpropylamine, 1-methylbutylamine, isopentylamine, neopentylamine, tert.-pentylamine, hexylamine, isohexylamine, 1,1-dimethylbutylamine, 1-methylpentylamine, 2-hydroxyethylamine, 2-hydroxypropylamine, 3-hydroxypropylamine, 2-hydroxy-1-methylethylamine, 2-, 3- or 4-hydroxybutylamine, 5-hydroxypentylamine, 6-hydroxyhexylamine, cyclopropylamine, cyclobutylamine, cyclopentylamine, cyclohexylamine, 1-, 2- or 3-methylcyclopentylamine, 1-, 2-, 3- or 4-methylcyclohexylamine, cycloheptylamine, cyclooctylamine, 2-phenylethylamine, 1-methyl-2-phenylethylamine, 1,1-dimethyl-2-phenylethylamine, 2phenylpropylamine, 3-phenylpropylamine, 1-methyl-3-phenylpropylamine, 2-, 3- or 4-phenylbutylamine, 2-(1-naphthyl)ethylamine, 2-(2-naphthyl)-ethylamine, 2-, 3- or 1-p-methoxyphenylethylamine, 2-(3,4-dimethoxyphenyl)-ethylamine, 2-(3,4-methylenedioxyphenyl)-ethylamine, aniline, o-, m- or p-toluidine, o-, m- or p-anisidine, o-, m- or p-aminophenol, o-, m- or p-chloroaniline, 3,4-dimethoxyaniline or 3,4-methxlenedioxyaniline. All alkyl portions in the R groups can correspondingly be selected from those mentioned above.

Examples of suitable aldehydes of the formula Z—CHOH—CHO are 2,3,4-trihydroxybutanals, such as the DL-, D- or L-forms of erythrose or threose, 2,3,4,5-tetrahydroxypentanals, such as the DL-, D- or L-forms of ribose, arabinose, xylose or lyxose, or 2,3,4,5,6-pentahydroxyhexanals, such as the DL-, D- or L-forms of allose, altrose, glucose, mannose, gulose, idose, galactose or talose. Examples of typical compounds of the formula II are N-R-2,3,4-trihydroxybutylamines, such as N-methyl-2,3,4-trihydroxybutylamines, N-R-2,3,4,5-tetrahydroxypentylamines, such as N-phenyl-2,3,4,5-tetrahydroxypentylamines, 2N-R-2,3,4,5,6-pentahydroxyhexylamines, such as N-phenyl2,3,4,5,6-pentahydroxyhexylamines, N-m-tolyl-2,3,4,5,6-pentahydroxyhexylamines, or N-methyl-, N-ethyl-, N-isopropyl- or N-tert.-butyl-2,3,4,5,6-pentahydroxyhexylamines, for example the N-R-glucamines derived from D-glucose (N-R-2S,3R,4R,5R,6-pentahydroxyhexylamines).

Examples of suitable carbonic acid derivatives are phosgene, dialkyl carbonates, such as dimethyl or diethyl carbonate, urea or carbonyldiimidazole.

The reaction of II with the carbonic acid derivative can be carried out in the absence or presence of an inert solvent, such as dimethylformamide (DMF), methanol or ethanol, at temperatures between about 0 and about 200°. Thus the reaction is preferably carried out with carbonyldiimidazole at about 0°-30° in DMF, or, with the other carbonic acid derivatives mentioned, at about 80°-150° without a solvent, but the addition of a base, such as NaOH, KOH, triethylamine or pyridine can be advantageous.

In some cases it is also possible to react further OH groups in II with the carbonic acid derivative, particularly if the latter is employed in excess. The carbonates thus formed can, however, be saponified readily under alkaline conditions with the formation of the desired compounds I.

Oxidative cleavage of the compounds (I), for example using HIO₄ or salts thereof, KMnO₄ or lead tetraacetate, and subsequent reduction of the 1-oxa-2-oxo-3-R-3-aza-5-formylcyclopentanes formed as intermediates leads to the corresponding 1-oxa-2-oxo-3-R-3-aza-5-hydroxymethylcyclopentanes (III), for example to toloxatone (R=m-tolyl). If compounds (I) wherein the C(5) atom has the S-configuration are used, the corresponding 1-oxa-2-oxo-3-R-3-aza5S-hydroxymethylcyclopentanes are obtained. The conversion of the 3-isopropyl compound into S-propranolol is known. The corresponding 5-chloromethyl, 5-bromomethyl, 5-acyloxymethyl (for example also 5-methanesulphonyloxymethyl or 5-p-toluenesulphonyloxymethyl), 5-alkoxymethyl or 5-aryloxymethyl derivatives can be prepared from the compounds III by reaction with SOCl₂ or PBr₃ or by esterification or etherification.

The compounds I can be used as intermediate products for the preparation of active compounds for medicaments, such as toloxatone or certain beta receptor blockers.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

1.62 g of carbonyldiimidazole are added to a solution of 2.71 g of N-m-tolyl-2S,3R,4R,5R,6-pentahydroxyhexylamine [IIa; m.p. 111°-114°, obtainable from D-glucose and m-toluidine/$H_2$/Pd-C in methanol/water] in 30 ml of DMF, and the mixture is stirred for 3 hours at 20°. After the mixture has been concentrated, imidazole is removed by distillation at 130°/0.2 bar. This gives 1-oxa-2-oxo-3-m-tolyl-3-aza-5S-(1R,2R,3R,4-tetrahydroxybutyl)-cyclopentane (Ia), which is purified by chromatography over silica gel. Rf 0.45 (90:10:5 methylene dichloride/methanol/acetic acid).

EXAMPLE 2

A mixture of 2.71 g of IIa, 10 ml of diethyl carbonate and 0.5 ml of triethylamine is stirred for 23 hours at 110°-120°. The mixture is evaporated and the residue is chromatographed over silica gel to give Ia.

EXAMPLE 3

A mixture of 2.71 g of IIa, 0.72 g of urea and 0.1 g of KOH is heated at 140°-150° for 2 hours. After cooling, the Ia obtained is chromatographed over silica gel.

EXAMPLE 4

A mixture of 2.71 g of IIa and 4 g of ethylene carbonate is heated at 100° for 3 hours. The mixture is evaporated and the residue is chromatographed over silica gel to give Ia.

EXAMPLES 5 to 20

The following 1-oxa-2-oxo-3-aza-5S-(1R,2R,3R,4-tetrahydroxybutyl)-cyclopentanes are obtained, analogously to Example 1, 2, 3 or 4, from N-methylglucamine, N-ethyl-glucamine, N-propylglucamine, N-isopropylglucamine, N-butylglucamine, N-isobutylglucamine, N-sec.-butylglucamine, N-tert.-butylglucamine, N-(2-hydroxyethyl)-glucamine, N-cyclohexylglucamine, N-phenylglucamine, N-p-methoxyphenylglucamine, N-(2-phenylethyl)-glucamine, N-(1,1-dimethyl-2-phenylethyl)-glucamine, N-[2-(3,4-dimethoxyphenyl)-ethyl]-glucamine and N-[2-(3,4-methylenedioxyphenyl)-ethyl]-glucamine respectively:
5. The 3-methyl derivative, m.p. 155°.
6. The 3-ethyl derivative.
7. The 3-propyl derivative.
8. The 3-isopropyl derivative, m.p. 163°.
9. The 3-butyl derivative.
10. The 3-isobutyl derivative.
11. The 3-sec.-butyl derivative.
12. The 3-tert.-butyl derivative, m.p. 158°.
13. The 3-(2-hydroxyethyl) derivative.
14. The 3-cyclohexyl derivative.
15. The 3-phenyl derivative.
16. The 3-p-methoxyphenyl derivative.
17. The 3-(2-phenylethyl) derivative.
18. The 3-(1,1-dimethyl-2-phenylethyl) derivative.
19. The 3-[2-(3,4-dimethoxyphenyl)-ethyl] derivative.
20. The 3-[2-(3,4-methylenedioxyphenyl)-ethyl] derivative.

EXAMPLE 21

1-oxa-2-oxo-3-isopropyl-3-aza-5R-(1R,2R,3R,4-tetrahydroxybutyl)-cyclopentane is obtained, analogously to Example 2, from N-isopropyl-2R,3R,4R,5R,6-pentahydroxyhexylamine (m.p. 122°; obtainable by treating a solution of D-mannose and isopropylamine in methanol/water with $H_2$ over 5% Pd-on-C for 3 hours at 50° and 3 bar).

EXAMPLE 22

100 mg of KOH powder are added to a solution of 2.37 g of N-tert.-butyl-2S,3R,4R,5R,6-pentahydroxyhexylamine (m.p. 112°; obtainable from D-glucose and tert.-butylamine/$H_2$/Pd-C) in 10 ml of diethyl carbonate, and the mixture is heated at 120° for 4 hours. The mixture is concentrated, the residue is taken up in ethanol and the solution is filtered. After cooling, the crystals which have been precipitated are filtered off with suction; m.p. 212°. The carbonate-ester groups which have been formed are saponified by warming the intermediate product briefly with a mixture of 3 ml of methanol, 3 ml of water and 0.5 g of KOH. After neutralization with hydrochloric acid; the solution is concentrated, the residue is extracted with methylene dichloride, and the extract is evaporated to give 1-oxa-2-oxo-3-tert.-butyl-3-aza-5S-(1R,2R,3R,4-tetrahydroxybutyl)-cyclopentane, m.p. 158°.

USE EXAMPLE 1

7.2 g of NaIO$_4$ are added at 20° to a suspension of 2.97 g of Ia in 180 ml of water, and the mixture is stirred for 30 minutes. The pH is then adjusted to 8 and 0.2 g of NaBH$_4$ are added in portions at 20°. After being stirred for a further 1.5 hours, the mixture is extracted with methylene dichloride, the extract is dried with Na$_2$SO$_4$ and evaporated and the residue is purified by chromatography. This gives 1-oxa-2-oxo-3-m-tolyl-3-aza-5S-hydroxymethylcyclopentane.

USE EXAMPLES 2 to 17

The following 1-oxa-2-oxo-3-aza-5S-hydroxymethylcyclopentanes are obtained, analogously to Use Example 1, by oxidative cleavage and subsequent reduction of the compounds mentioned in Examples 5 to 20:
2. The 3-methyl derivative.
3. The 3-ethyl derivative.
4. The 3-propyl derivative.
5. The 3-isopropyl derivative, m.p. 55°-58°.
6. The 3-butyl derivative.
7. The 3-isobutyl derivative.
8. The 3-sec.-butyl derivative.
9. The 3-tert.-butyl derivative.
10. The 3-(2-hydroxyethyl) derivative.
11. The 3-cyclohexyl derivative.
12. The 3-phenyl derivative.
13. The 3-p-methoxyphenyl derivative.
14. The 3-(2-phenylethyl) derivative.
15. The 3-(1,1-dimethyl-2-phenylethyl) derivative.
16. The 3-[2-(3,4-dimethoxyphenyl)-ethyl] derivative.
17. The 3-[2-(3,4-methylenedioxyphenyl)-ethyl]derivative.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1-oxa-2-oxo-3-R-3-aza-5-Z-cyclopentane wherein:

R is alkyl or hydroxyalkyl each of 1–6 C atoms, cycloalkyl or alkylcycloalkyl each of 3–8 total C atoms, hydrocarbon aryl or hydrocarbon aralkyl each of 6–15 total C atoms or hydrocarbon aryl or hydrocarbon aralkyl each of 6–15 C total atoms and each monosubstituted or disubstituted in the aryl group by $C_{1-6}$-alkyl, $C_{1-6}$-alkoxy, OH, Cl or a combination thereof, and/or monosubstituted by methylenedioxy, Z is $-(CHOH)_n-H$ and n is 2, 3, 4 or 5.

2. A compound of claim 1, wherein R is alkyl.
3. A compound of claim 1, wherein R is hydroxyalkyl.
4. A compound of claim 1, wherein R is cycloalkyl.
5. A compound of claim 1, wherein R is alkylcycloalkyl.
6. A compound of claim 1, wherein R is hydrocarbon aryl.
7. A compound of claim 1, wherein R is hydrocarbon aralkyl.
8. A compound of claim 1, wherein R is substituted hydrocarbon aryl.
9. A compound of claim 1, wherein R is alkyl or hydroxyalkyl each of 1–6 C atoms, cycloalkyl or alkylcycloalkyl each of 3–8 total C atoms, hydrocarbon aryl or hydrocarbon aralkyl each of 6–15 total C atoms or hydrocarbon aryl or hydrocarbon aralkyl each of 6–15 C total atoms and each substituted in the aryl group by a methyl group, one or two methoxy groups or a methylenedioxy group.
10. A compound of claim 1, wherein n is 2.
11. A compound of claim 1, wherein n is 5.
12. 1-Oxa-2-oxo-3-methyl-3-aza-5-(1,2,3,4-tetrahydroxy-butyl)-cyclopentane, a compound of claim 1.
13. 1-Oxa-2-oxo-3-isopropyl-3-aza-5-(1,2,3,4-tetrahydroxy-butyl)-cyclopentane, a compound of claim 1.
14. 1-Oxa-2-oxo-3-tert.-butyl-3-aza-5-(1,2,3,4-tetrahydroxy-butyl)-cyclopentane, a compound of claim 1.
15. 1-Oxa-2-oxo-3-m-tolyl-3-aza-5-(1,2,3,4-tetrahydroxy-butyl)-cyclopentane, a compound of claim 1.

* * * * *